US008752548B2

(12) United States Patent (10) Patent No.: US 8,752,548 B2
Larsson et al. (45) Date of Patent: Jun. 17, 2014

(54) PATIENT VENTILATION SYSTEM WITH A GAS IDENTIFICATION UNIT

(75) Inventors: Åke Larsson, Järfälla (SE); Lars Wallen, Spånga (SE); Carl Erik Troili, Danderyd (SE)

(73) Assignee: Maquet Critical Care AB, Solna (SE)

( * ) Notice: Subject to any disclaimer, the term of this patent is extended or adjusted under 35 U.S.C. 154(b) by 1049 days.

(21) Appl. No.: 12/666,799

(22) PCT Filed: Jun. 28, 2007

(86) PCT No.: PCT/EP2007/056483
§ 371 (c)(1),
(2), (4) Date: Jun. 8, 2010

(87) PCT Pub. No.: WO2009/000328
PCT Pub. Date: Dec. 31, 2008

(65) Prior Publication Data
US 2010/0269821 A1   Oct. 28, 2010

(51) Int. Cl.
*F16K 11/00* (2006.01)
*G05D 11/02* (2006.01)
*G05B 1/00* (2006.01)

(52) U.S. Cl.
USPC ............. 128/204.22; 128/203.25; 128/205.11

(58) Field of Classification Search
USPC ............. 128/204.22, 203.12, 203.13, 203.25, 128/204.21, 205.11, 202.22, 203.14, 128/203.29, 205.23, 205.25; 600/529, 532, 600/537, 538
See application file for complete search history.

(56) References Cited

U.S. PATENT DOCUMENTS

| 5,231,591 | A  |   | 7/1993  | Flewelling et al. |
|-----------|----|---|---------|-------------------|
| 5,429,123 | A  | * | 7/1995  | Shaffer et al. ............ 128/204.23 |
| 5,515,295 | A  | * | 5/1996  | Wang .............................. 702/45 |
| 5,627,323 | A  | * | 5/1997  | Stern .......................... 73/861.28 |
| 5,730,119 | A  |   | 3/1998  | Lekholm |
| 6,089,229 | A  | * | 7/2000  | Bathe et al. ............. 128/204.21 |
| 6,709,405 | B2 | * | 3/2004  | Jonson ......................... 600/538 |
| 6,912,907 | B2 | * | 7/2005  | Fujimoto ....................... 73/597 |
| 2003/0106554 | A1 | * | 6/2003 | de Silva et al. .......... 128/204.22 |
| 2004/0149285 | A1 |   | 8/2004 | Wallen |
| 2004/0211244 | A1 |   | 10/2004 | Cardelius et al. |
| 2006/0290525 | A1 | * | 12/2006 | Andersen et al. ............. 340/632 |
| 2007/0125374 | A1 | * | 6/2007 | Smith et al. .............. 128/203.12 |

FOREIGN PATENT DOCUMENTS

| DE | 296 13 243 U1 | 11/1996 |            |
|----|---------------|---------|------------|
| EP | 1441222 A2 *  | 7/2004  | ............. G01N 29/02 |
| WO | WO 88/04409   | 6/1988  |            |

* cited by examiner

*Primary Examiner* — Justine Yu
*Assistant Examiner* — Christopher Miller
(74) *Attorney, Agent, or Firm* — Schiff Hardin LLP

(57) ABSTRACT

A patient ventilation system has a flow regulating and gas mixing arrangement connected to an inspiratory channel of the system from which a gas mixture containing oxygen and at least a second gas is delivered to the system's proximal tubing. The proximal tubing further is connected to an expiratory channel and is connectable to a patient. The system further has at least two gas inlets connected to the flow regulating and mixing arrangement, and a gas identification unit in which the at least second gas supplied to the system via one of the gas inlets can be identified. By actively measuring a value that is dependent on the characteristics of the delivered gas, and by correcting the calibration of the flow regulating and gas mixing arrangement and/or the flow meter(s) based on this value, both safety and flow regulation in the system are enhanced.

12 Claims, 6 Drawing Sheets

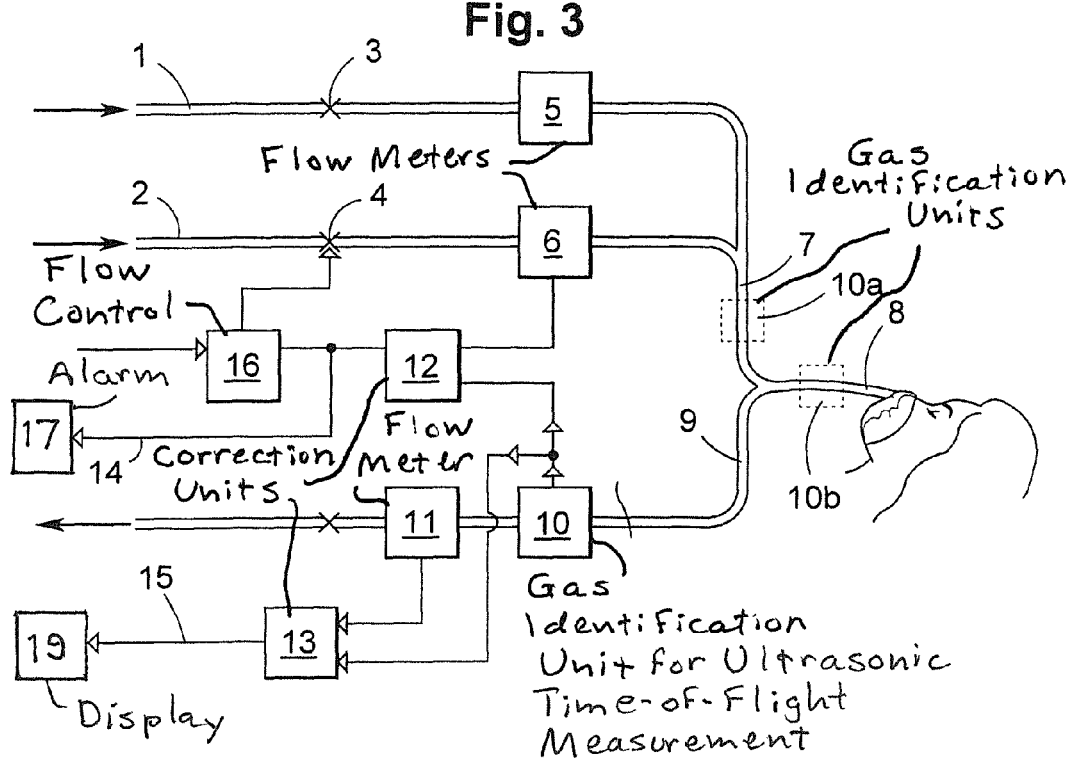
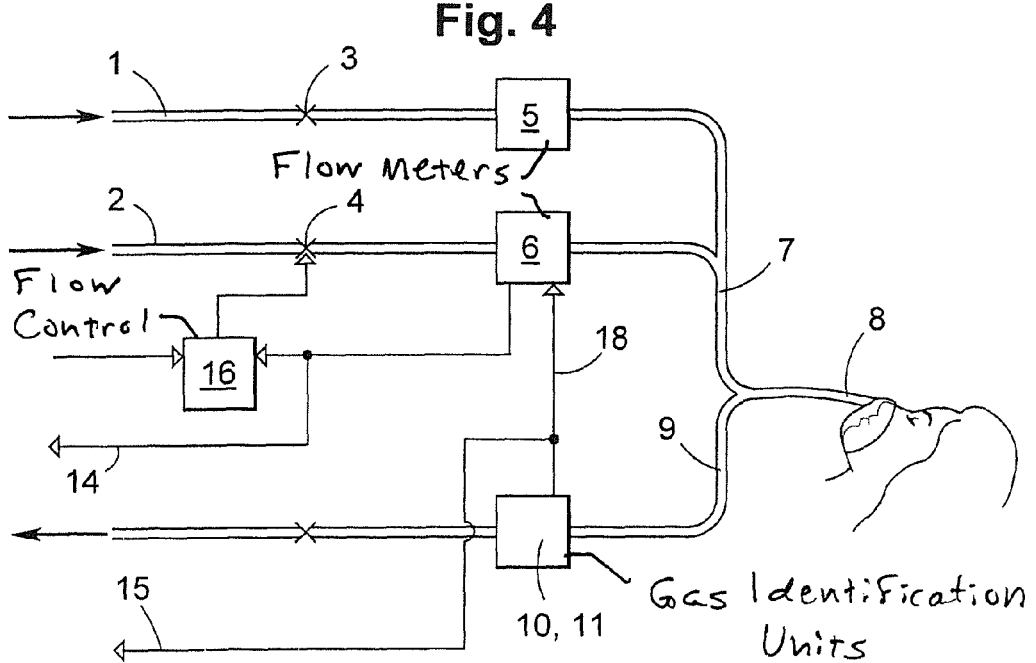

PATIENT VENTILATION SYSTEM WITH A GAS IDENTIFICATION UNIT

BACKGROUND OF THE INVENTION

1. Field of the Invention

The present invention relates to a patient ventilation system of the type having flow regulating and gas mixing means connected to an inspiratory channel of the system wherefrom a gas mixture comprising oxygen and at least a second gas is delivered to the system's proximal tubing, the proximal tubing being connected to an expiratory channel and connectable to a patient, and at least two gas inlets connected to said flow regulating and mixing means, and gas identification means by which said at least second gas supplied to the system via one of the gas inlets can be identified.

2. Description of the Prior Art

A system of the above type is described in EP 1 455 876 B1.

Patient ventilation systems are employed in the administration of breathing gas to a patient, particularly in a hospital environment, and operate to control either or both the amount and the composition of the administrated breathing gas. As such, the term "ventilation system" shall encompass in the present context ventilators, respirators and anesthesia machines as well as on-demand type face masks employed in medical environments.

Patients in need of frequent respiratory treatment often show a severe increase in airway resistance. To overcome that resistance, a certain gas pressure is needed for moving gas into and out of the lungs of the patient. The pressure in the airway is directly related to the dynamic pressure gradient during the respiratory cycle, the flow rate of the gas, the density and viscosity of the gas, and the caliber and length of the airway.

It is well known to mix air with oxygen to increase the overall oxygen concentration delivered to the patient. To decrease the pressure required for moving gas through the airways, air can be substituted by "heliox", a mixture of helium and oxygen. As an inert gas, helium does not participate in any biochemical process of the body. However, as helium is the second lightest gas, it decreases the density and by that the required driving pressure. Typically, helium is mixed with at least 21% oxygen but depending on the specific conditions of the patient, this mixture can be altered.

Prior art ventilation systems normally have at least two gas inlets, one of which is connected to an oxygen source and the other to a second gas source such as an air source or a heliox source. If heliox is used, the distribution between helium and oxygen in the heliox mixture is typically 80% helium and 20% oxygen (heliox 80/20), or 70% helium and 30% oxygen (heliox 70/30). These external gas sources may be provided locally by pressurized bottles. Typically, there are often more gas supplies available for connection to the gas inlets than are required and care must be taken to ensure that the correct supplies are connected, especially as conventional gas sources are supplied with standardized pneumatic connection terminals. The prior art mentioned above discloses a gas identifier, which comprises a voltage divider adapted to provide an electrical interface to the ventilation system and a lookup table. The voltage divider includes a resistor having a resistance value unique for each gas supply. For a specific gas supply, a corresponding voltage drop will result as measured across the resistor. The lookup table comprises a list of voltage drops for the various gases, so that the gas mapping with the voltage drop is obtained from the lookup table.

With such an identification system, there may be an uncertainty as to whether the correct voltage divider has been introduced or not. Therefore, the safety of such a system is deficient and barely provides more certainty than manually identifying the gas supply by simply looking at it and making the correct input to the ventilation system via the interface. In both cases and having in mind the stress situation in an ICU, there is no absolute knowledge about the gas, which actually is delivered to the ventilation system and there is no check up or safety control.

As is also known, e.g. from the prior art mentioned above, flow meters provide output signals which are dependent on the type of gas, i.e. if a flow meter is calibrated for measuring air, the meters output signal would deviate from the actual flow for another gas type like heliox 80/20. This is true even for other gases like zenon or other gas mixtures. The prior art therefore suggests means for correcting the calibration of any flow meter based on gas supply, which is identified in the above described way.

To increase the safety of any gas supply to a patient ventilation system, EP 1 441 222 A2 discloses monitoring means using a acoustic transceiver detecting the amplitude of the emitted acoustic energy propagated through a measurement chamber and generating a control signal from a comparison of the detected signal with a reference signal for the target gas, and generating a control signal to inhibit the gas flow through the system if the wrong gas is supplied. This prior art gives no hint to use the detected signal for anything else but inhibiting the gas flow.

It is further known to use an oxygen sensor, e.g. an oxygen cell, to measure the oxygen concentration in the ventilation system. Such an oxygen sensor cannot be used to identify other gases or gas mixtures like air or heliox to be mixed with pure oxygen.

SUMMARY OF THE INVENTION

An object of the present invention is to improve the safety of the identification of any gas or gas mixture connected to the ventilation system via a gas inlet and to provide an automatic correction of the flow meter(s) based on online measured gas identification.

It is another object of the invention to ensure that any possible human mistake in connecting a gas source to an inlet has no influence for the correct functioning of the system.

It is another object of the invention to generate an alarm signal in case the intended and programmed gas is not detected or a deviating gas mixture is detected.

To further simplify the overall ventilation system, it is another object of the invention to use already existing components in the ventilation system for the identification purpose.

The above object is achieved in accordance with the present invention by a patient ventilation system having a regulating and gas mixing arrangement connected to an inspiratory channel of the system, from which a gas mixture containing oxygen and at least a second gas is delivered to the proximal tubing of the system. The proximal tubing further is connected to an expiratory channel and is connectable to a patient. The system further has at least two gas inlets connected to the flow regulating and mixing arrangement, and a gas identification unit in which the at least second gas, supplied to the system via one of the gas inlets, is identified. By actively measuring a value that is dependent on a characteristic of the delivered gas, and by correcting the calibration of the flow regulating and gas mixing arrangement and/or a flow meter based on this value, both safety and flow regulation in the system are enhanced.

There are a number of characteristics which differ for different types of gases or gas mixtures, e.g. the speed of sound through the gas or the thermal conductivity. The speed of sound can be measured with an ultrasonic transducer and the thermal conductivity can be measured with a heated thermistor or thermal resistor. However, the invention is not limited to the use of these particular gas characteristics for identifying the gas or gas mixture. Any properties or characteristics that differ from gas to gas, or gas mixture to gas mixture, to an extent that is measurable with the gas identification unit, may be used. Since the flow rate measured by conventional flow meters also depends on the gas characteristics, the present invention provides means for automatically correcting the calibration of any flow regulating and gas mixing units and/or flow meters in the ventilation system depending on the online measurement of the type of gas or gas mixture connected to the gas inlet. Since the gas supply is actively measured and identified, the system is not limited to gas bottles with a predefined gas mixture, for example Heliox 70/30 or 80/20, as provided from the suppliers, but will function properly with an arbitrary gas mixture. Thus the system will function very well even in rebreathing setups where expensive gases like Zenon are used, and where the expired gas is directly reused after $CO_2$ has been removed by a filter. In such a situation, the supplied gas will differ in its mixture over time, but the system will always identify the mixture and correct the flow regulation and gas mixing units and/or flow meters accordingly. In addition, the ventilation system will detect if an erroneous gas bottle is unintentionally connected to the ventilation system. Thereby the ventilation system according to the present invention is less vulnerable to human errors than most prior art ventilation systems.

The gas identification unit can be arranged anywhere in the gas flow after the gas inlet, i.e. in the inspiration channel, the proximal tubing, which is connectable to a patient, or the expiration channel. Depending on the actual placement of the identification unit, other factors like $CO_2$ or humidity may have to be taken into account. None the less, identification is possible at all places.

In a preferred embodiment of the invention, the output signal from the identification unit is displayed on an interface connectable to the ventilation system, to show the user of the system which gas has been identified.

In another preferred embodiment of the invention, the output signal of the identification unit will generate an alarm if the connected gas is not identified or if the identifies gas or gas mixture is not allowed, e.g. if 100% helium is identified.

In yet another preferred embodiment of the invention, flow meters already existing in the system are simultaneously used as a gas identification unit, preferably flow meters using transit time technology. By that, the number of components in the system can be minimized.

BRIEF DESCRIPTION OF THE DRAWINGS

FIG. 3 shows a first embodiment of a ventilation system with identification unit for gases connected to a gas inlet.

FIG. 4 shows a second embodiment of such a system.

DESCRIPTION OF THE PREFERRED EMBODIMENTS

Figure 1:
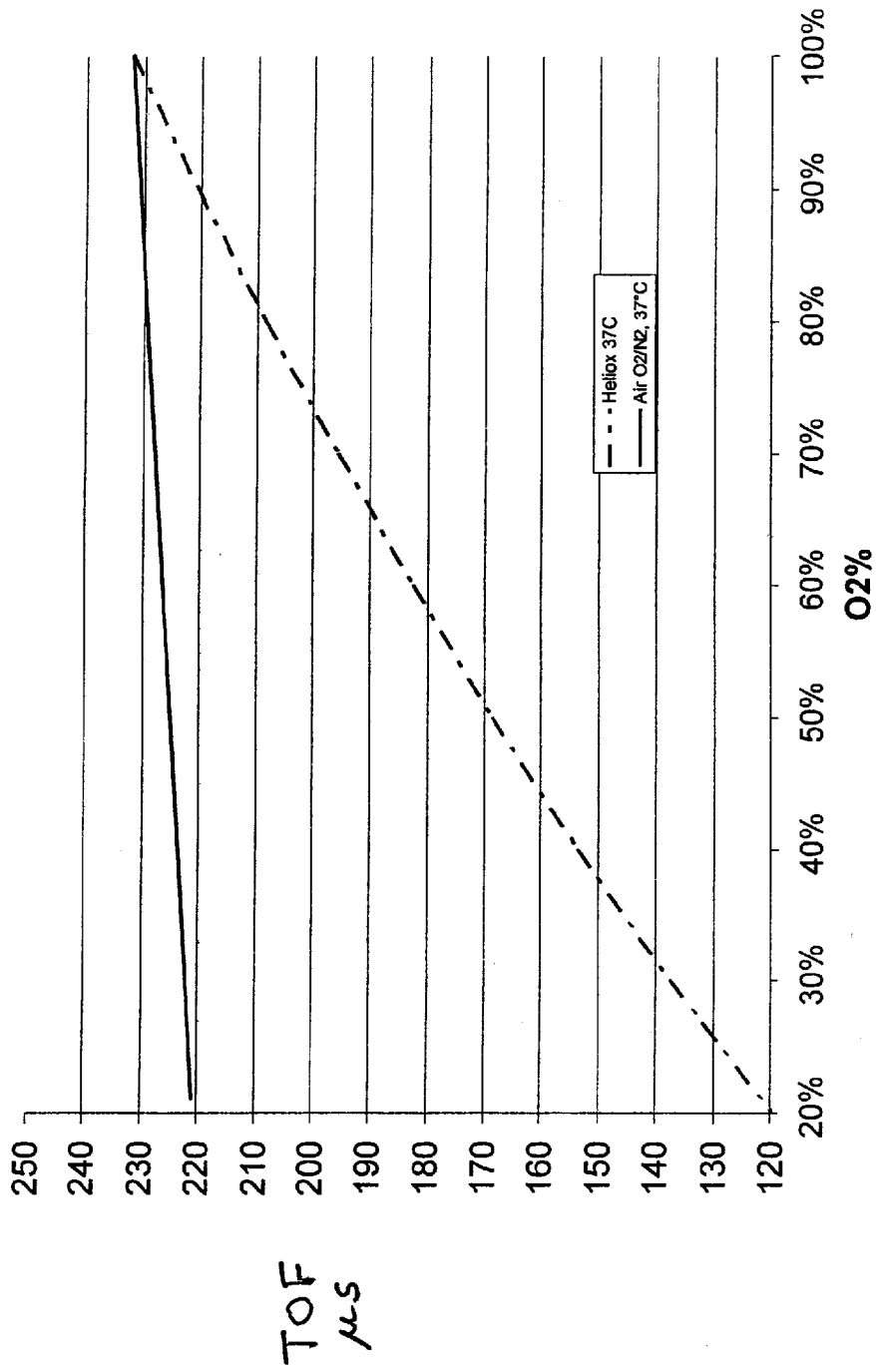
FIG. 1 shows the principal of the gas identification using transit time technology.

FIG. 1 shows the principle of the gas identification using e.g. an ultrasound transceiver which measures the time of flight (TOF) for a sound pulse passing through the gas to be identified or, if it is done in the expiration line of the system, the expired gas including the gas to be identified. In this latter case, humidity and $CO_2$ concentration can be estimated. FIG. 1 shows the TOF over the $O_2$ concentration in percent for air as a solid line and for heliox as a broken line, starting on the left side of the diagram with 20% $O_2$. Since helium concentration has a big influence on the speed of sound, there is a great difference in the time of flight between the sound pulses traversing heliox and the sound pulses traversing an equal distance in air. With a temperature of 37 degrees Celsius, a dry gas, and a specific measurement setup, the TOF for the sound pulse is approximately 122 µs in heliox 79/21 (21% $O_2$), and approximately 222 µs in air. As can be seen from this diagram, increasing the $O_2$ concentration changes the TOF for air only slightly, but for heliox substantially. Over the interval between 21% $O_2$ and 100% $O_2$ the TOF for heliox varies with 110 µs. As a result, the TOF measurements are equal to having a sensitive helium concentration meter and the composition of heliox, i.e. the mixture of helium and oxygen, can be identified with great accuracy. If the measured TOF stays within predefined limits, e.g. ±5 µs from the expected value for the gas mixture to be supplied, then the gas mixture has been identified. A greater deviation indicates that the wrong gas mixture has been connected to the gas inlet or that the identification does not work properly.

Figure 2:
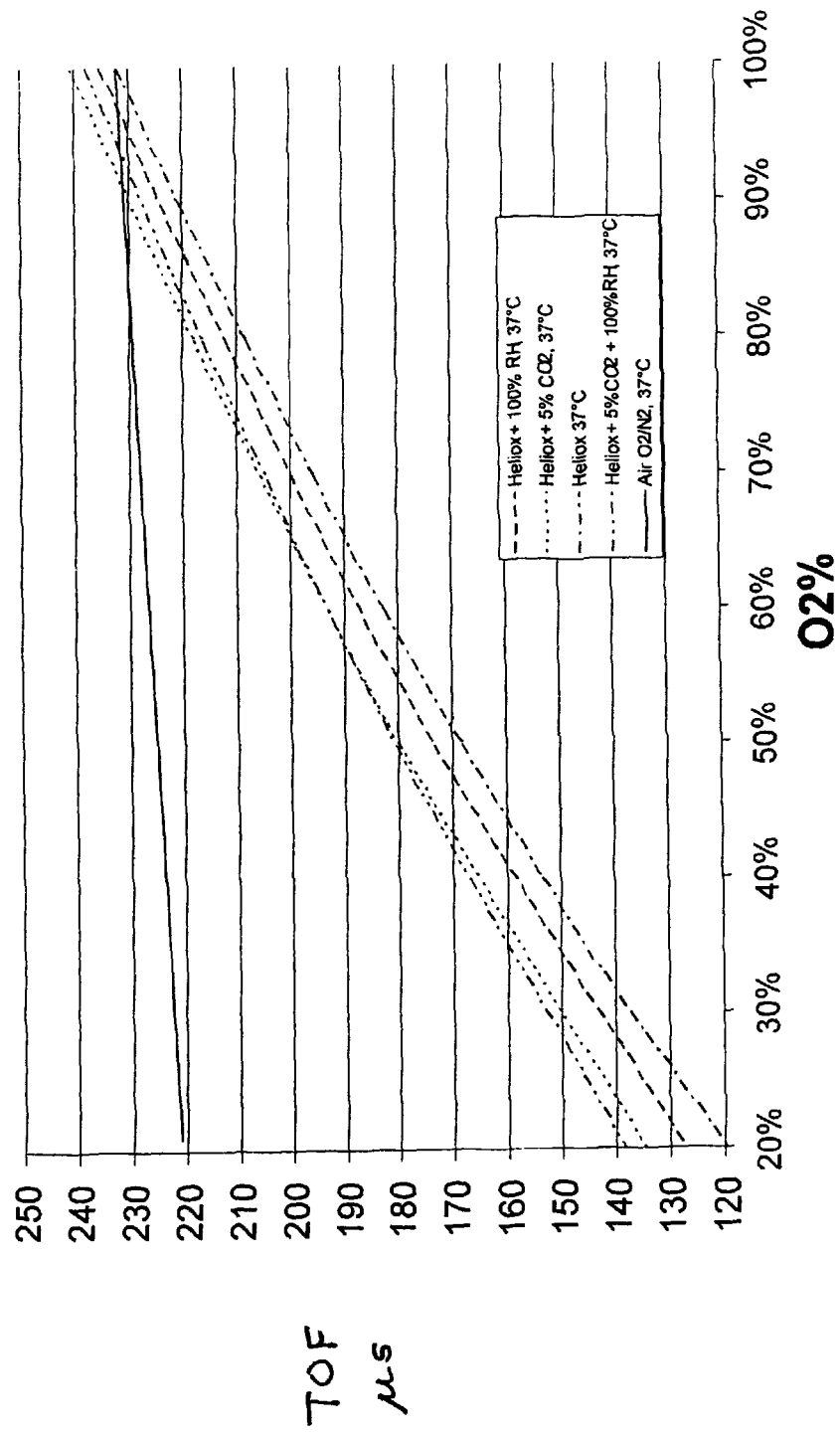
FIG. 2 shows the same principal for additional gas mixtures and conditions.

FIG. 2 shows the same diagram as FIG. 1 for compositions where heliox is mixed with 5% $CO_2$ and/or has 100% relative humidity (RH). As can be seen from this diagram, if the $CO_2$ concentration and/or humidity is known or can be estimated, the system still functions in a satisfactory way to identify the correct gas mixture.

Figure 7:
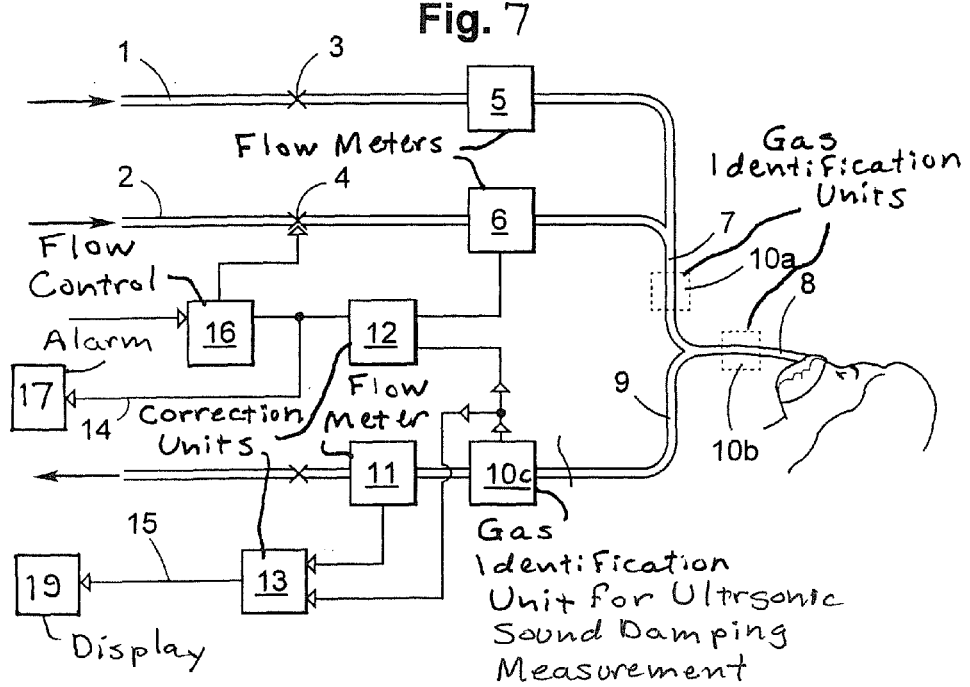
FIG. 7 shows a second embodiment of a ventilation system with an identification unit for gases connected to a gas inlet.
Figure 8:
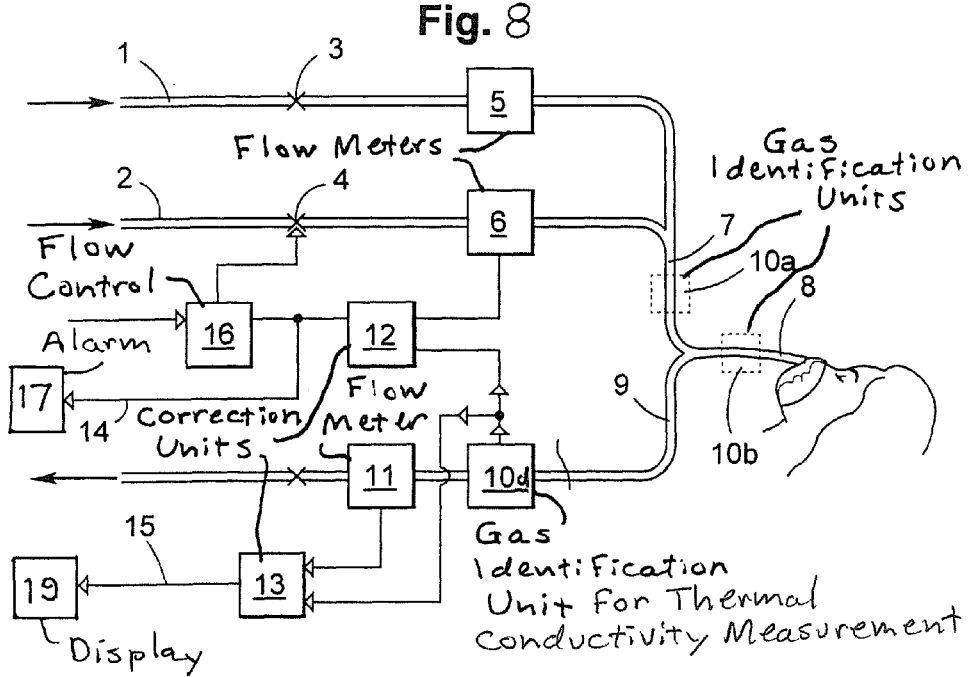
FIG. 8 shows a third embodiment of a ventilation system with an identification unit for gases connected to a gas inlet.

The gas identification unit 10 in the embodiment shown in FIG. 3 operates by using an ultrasound transducer to implement an ultrasonic time-of-flight measurement of the second gas. In the embodiment of FIG. 7, a gas identification unit 10c is provided that has a transducer to implement an ultrasonic sound damping measurement. In the embodiment shown in FIG. 8, the gas identification unit 10d implements a thermal conductivity measurement of the second gas.

FIG. 3 shows a first embodiment of a patient ventilation system with gas identification unit for gases connected to a gas inlet. The system has two gas inlets 1 and 2, one for oxygen and one for air/heliox. From the inlets, the gases are let via inspiratory valves 3 and 4 and flow meters 5 and 6 to an inspiration channel 7, and further via a proximal tubing 8 to the airways of a patient. The expired gas passes through the expiration channel 9, gas identification unit 10 and a flow meter 11. The gas identification unit 10 can as well be arranged in the inspiration channel or the proximal tubing, without deviating from the general principal of the invention. Gas identification units 10a and 10b are depicted in these places in dashed lines.

In a ventilation system without gas identification means, the output signal from the flow meter 6 is fed to a flow control 16 as actual value. The flow control 16 compares this value with a set value and generates a control signal for the inspiration valve 2. The same closed loop flow control is provided for the O2 supply, but not depicted in the figure.

According to the present invention, the gas identification unit 10 generates a signal representative for the measured gas mixture, e.g. air 21/79, heliox 20/80 or heliox 30/70. This signal is fed to correction units 12 and 13 for correcting the flow value directly measured by the flow meters 6 or 11. Normally, the flow meters are calibrated for air and their output signal would deviate from the actual value for other gases like heliox. The correcting units 12 or 13 compensate for such a deviation and make sure, that the flow control 16 receives a corrected actual value. In addition, the corrected flow signals are fed to an alarm 17 and/or a display 19, as indicated by arrows 14 and 15.

In this embodiment, the correction of the flow takes place in the correction units 12, 13. Without deviating from the present invention, these units 12, 13 can be part of the flow meters 6, 11 so that the output signal from the gas identification unit 10 corrects the calibration of the flow meters 6, 11.

FIG. 4 shows a second embodiment of the present invention, in which the same reference numerals as in FIG. 3 are used for similar components.

The only but important difference between the embodiments shown in FIG. 3 and FIG. 4 is a specific flow meter 11, which uses transit time technology such as ultra sound propagation to measure the flow. This measurement technology can simultaneously be used to identify the gas passing through the flow meter 11, either by utilizing the speed of sound or the damping of a sound pulse traversing the gas flow, as is generally known in the art. As an advantage, no separate gas identification means is necessary. The output signal from this combined gas identification means/flow meter 10, 11 is fed via line 18 to the flow meter 6 to correct its calibration. It is also possible to include a unit for correction between the flow meter 6 and the flow control 16 as in FIG. 1. Again, the flow meter 6 could be combined with the gas identification means if the technology for measuring the flow is suitable to measure a value, which depends on a characteristic of the gas to be identified. As mentioned before, other characteristics of the gas to be identified, e.g. the thermal conductivity thereof, could also be used in the identification process without deviating from the principle of the invention.

Figure 5:
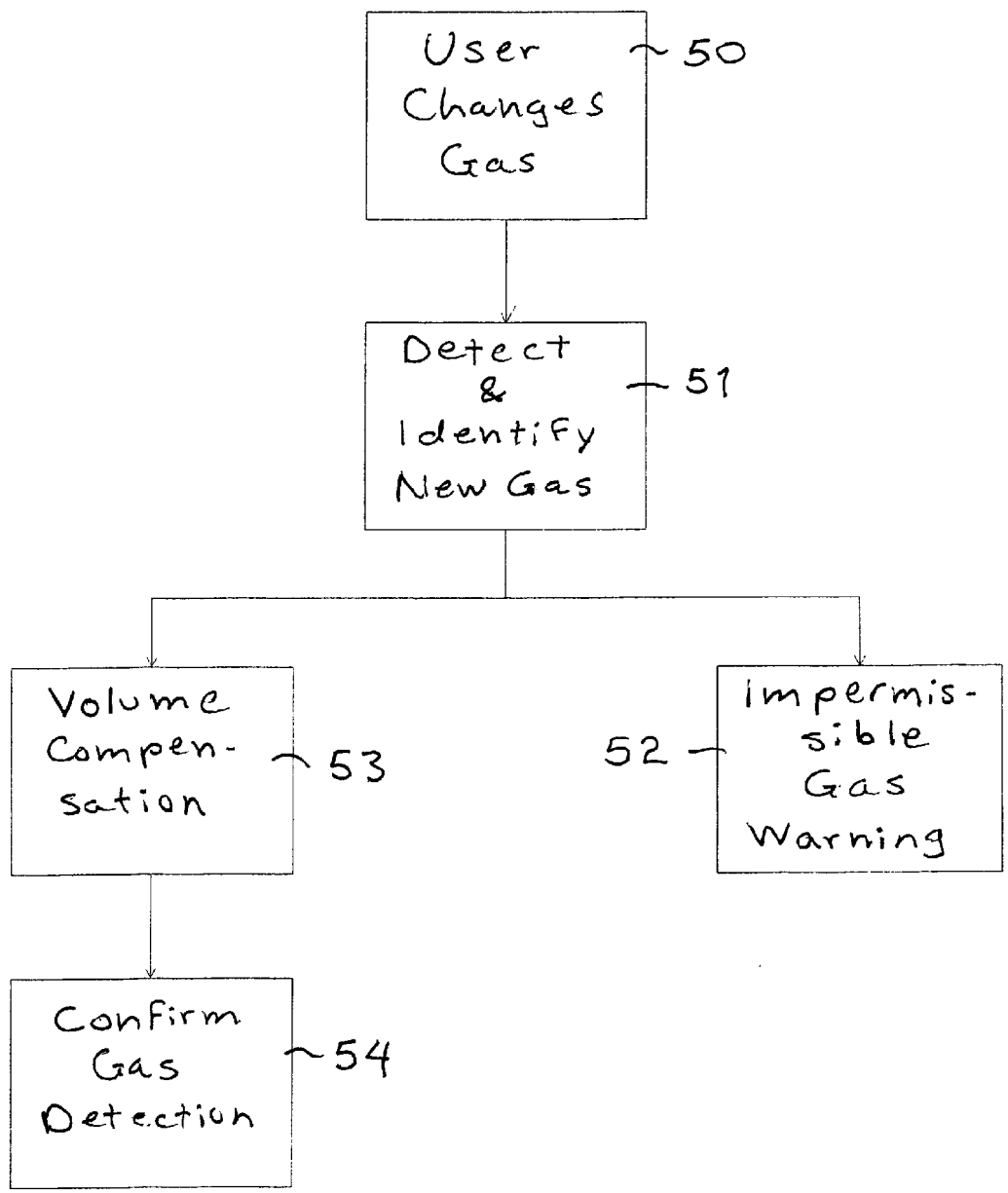
FIG. 5 shows a flow diagram for a gas exchange in a standby situation.
Figure 6:
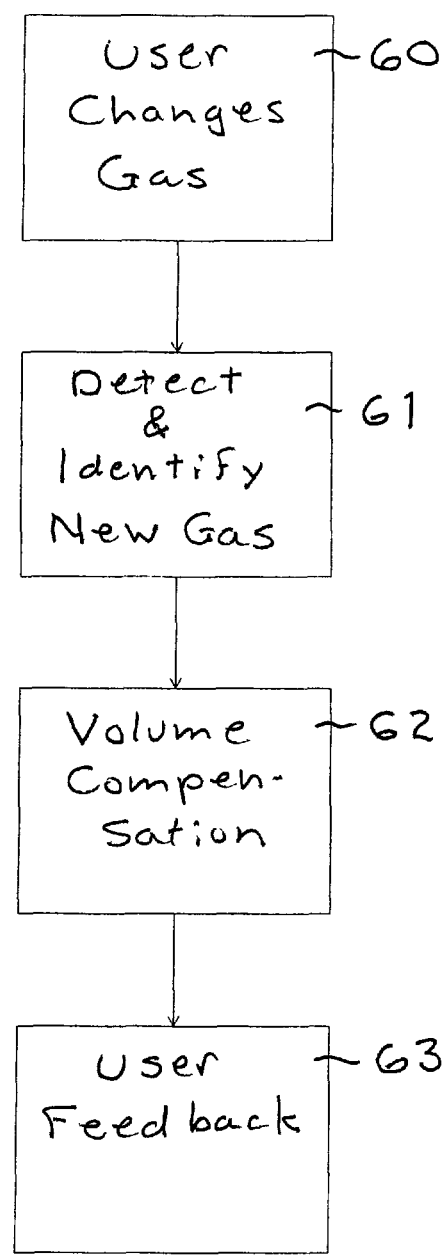
FIG. 6 shows a flow diagram for a gas exchange during ventilation.

In all embodiments, the possibility to generate an alarm if the identified gas deviates from the gas the user has chosen, or if no gas is identified, increases the overall safety of the ventilation system. The display on an interface facilitates the understanding of what is going on in the system. Another advantage of this automatic gas identification and flow correcting system according to the invention lies in the possibility to check the gas supply in a pre-use check when a new gas supply is connected to one gas inlet under standby, or even during ventilation. FIGS. 5 and 6 show possible flow diagrams for these two cases.

FIG. 5 illustrates a flow diagram for a gas exchange in a standby situation. In step 50, a user changes the gas in the ventilation system and, in step 51, the gas identification units 10, 10a, 10b detects and identifies the new gas. If the detected gas or gas mixture is not allowed, the procedure proceeds to step 52 in which the system warns the user by means of a suitable alarm signal, e.g. by displaying an alarm symbol on the interface or by generating a sound alarm. If, on the other hand, the detected gas or gas mixture is allowed, the procedure proceeds to step 53 in which the system compensates the set volume, i.e. the breathing gas volume provided to a patient during ventilation, in dependence of the properties of the new gas. Finally, in step 54, the system confirms the gas detection by, e.g., a notification displayed on the interface, and further prompts the user to review the ventilation settings in order to ensure a correspondence between the ventilator settings and the new gas.

FIG. 6 shows a flow diagram for a gas exchange during ventilation. The procedure is identical to the procedure illustrated in FIG. 5, in the case where an allowed gas or gas mixture is detected by the gas identification units 10, 10a, 10b. Consequently, in step 60, a user changes the gas used in the ventilation system whereupon the system detects the new gas in step 61. In step 62, the system compensates the set volume based on the detected gas and, in step 63, the system gives the user feedback on the gas detection and prompts the user to review the ventilator settings.

We claim as our invention:

1. A patient ventilation system comprising:
    a breathing circuit comprising an inspiratory channel and an expiratory channel adapted for connection to a patient;
    a gas mixing arrangement connected to said inspiratory channel to deliver a gas mixture comprising oxygen and a second gas to said patient via said inspiratory channel, said gas mixing arrangement being configured to regulate an amount of said second gas in said gas mixture;
    at least two gas inlets connected to said gas mixing arrangement, said second gas being supplied to said gas mixing arrangement via one of said gas inlets;
    a gas identification unit configured to detect an identity of said second gas by actively measuring a value of an identity-indicating characteristic of said second gas;
    a flow meter through which said second gas flows; and
    a correction unit connected to said gas identification unit that generates a correction value dependent on the detected identity of said second gas by said gas identification unit, said correction unit supplying said correction value to said flow meter to calibrate said flow meter to accurately detect flow of said second gas having the detected identity.

2. A patient ventilation system as claimed in claim 1 wherein said gas identification unit is configured to ultrasonically measure a speed of sound through said second gas.

3. A patient ventilation system as claimed in claim 1 wherein said gas identification unit is configured to ultrasonically measure a damping of a sound pulse through said second gas.

4. A patient ventilation system as claimed in claim 1 wherein said gas identification unit is configured to measure the thermal conductivity of said second gas.

5. A patient ventilation system as claimed in claim 1 wherein said gas identification unit is located in said inspiratory channel.

6. A patient ventilation system as claimed in claim 1 wherein said gas identification unit is located in said expiratory channel.

7. A patient ventilation system as claimed in claim 1 wherein said breathing circuit comprises proximal tubing adapted for direct connection to a patient, and wherein said gas identification unit is located in said proximal tubing.

8. A patient ventilation system as claimed in claim 1 wherein said gas identification unit comprises a gas identifying flow meter configured with gas identification capability.

9. A patient ventilation system as claimed in claim 8 wherein said gas identifying flow meter comprises an ultrasonic transducer configured for gas identification.

10. A patient ventilation system as claimed in claim 8 wherein said flow meter comprises a thermistor configured for gas identification.

11. A patient ventilation system as claimed in claim 1 comprising a display connected to said gas identification unit, said display being supplied with a signal from said gas identification unit identifying said second gas, and being configured to display a visual indication of said signal from said gas identification unit.

12. A patient ventilation system as claimed in claim 1 comprising an alarm generator connected to said gas identification unit, said alarm generator being configured to generate a humanly perceptible alarm signal if the second gas identified by said gas identification unit deviates from a predetermined gas.

\* \* \* \* \*